United States Patent [19]

Korbonits et al.

[11] Patent Number: 4,960,773
[45] Date of Patent: Oct. 2, 1990

[54] XANTHINE DERIVATIVES

[75] Inventors: Dezsö Korbonits; Gergely Héja; Maria Szomor, all of Budapest; Emil Minker, Szeged, all of Hungary

[73] Assignee: Chinoin Gyogyszer- es Vegyeszeti Termekek Gyara RT., Budapest, Hungary

[21] Appl. No.: 266,438

[22] Filed: Nov. 2, 1988

[30] Foreign Application Priority Data

Nov. 2, 1987 [HU] Hungary ............................ 4905/87

[51] Int. Cl.$^5$ ........................................ C07D 473/06
[52] U.S. Cl. .............................. 514/234.21; 514/265; 544/118; 544/273; 544/267; 544/272; 544/276
[58] Field of Search ............... 544/118, 273, 267, 272, 544/276; 514/265, 234.2

[56] References Cited

U.S. PATENT DOCUMENTS 4,565,817  1/1986  Korbonits et al. .................. 514/263
4,840,949  6/1989  Korbonits et al. ............... 514/234.2

*Primary Examiner*—John M. Ford
*Attorney, Agent, or Firm*—Herbert Dubno; Jonathan Myers

[57] ABSTRACT

The present invention relates to new compounds of Formula I

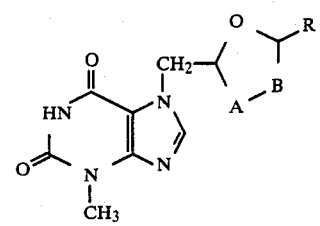

and physiologically acceptable salts thereof wherein A and B stand for oxygen or —$CH_2$ group with the proviso that if A stands for oxygen, then B stands for —$CH_2$ group and R stands for hydrogen and, if A represents a —$CH_2$ group, then B stands for oxygen, R stands for a —$CH_2Q$ group wherein Q stands for hydrogen, and pyrrolidino, piperidino or morpholino and a process for the preparation thereof and pharmaceutical compositions containing as active ingredient a compound of the Formula (I) or a physiologically acceptable salt thereof.

8 Claims, No Drawings

XANTHINE DERIVATIVES

The present invention is directed to new xanthine derivatives of the Formula I,

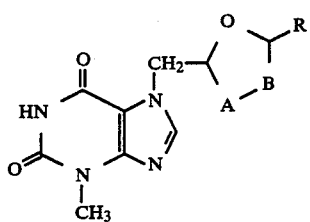

pharmaceutically acceptable salts thereof, a process for the preparation thereof and pharmaceutical compositions containing compounds of the Formula I as active ingredients.

The compounds, of the Formula I are suitable for treating diseases of the respiratory system and first of all they can be used as antitussive agents.

In the Formula I, A and B stand for O-atom or —$CH_2$— group with the proviso that if A stands for oxygen, then B stands for a —$CH_2$—group, R stands for hydrogen atom, if A stands for a —$CH_2$—group then B represents oxygen, R stands for a —$CH_2$—Q group wherein Q stands for hydrogen, pyrrolidino, piperidino or morpholino.

BACKGROUND OF THE INVENTION

It is known that theophylline derivatives substituted in position 7 by a dioxolanyl-methyl group have antitussive activity. Such results are disclosed in the German open application No. 2 827 497 and in French Patent Specification No. 8 107 075.

The pharmacological properties of 2-[(theophylline-7-yl)methyl]-1,3-dioxolane mentioned in the above patent document have been disclosed in detail (Il Farmaco, Ed. Sci. 36. Vol. 3., 201 1981; Drugs of the Future, 1982, 301).

DESCRIPTION OF THE INVENTION

We have now found that the compounds of the Formula I have a more intensive antitussive activity than the dioxolane-methyl-theophyllines mentioned above. The difference in the chemical structure between the compounds of the Formula I and the analogous theophylline derivatives disclosed in the above patent documents or literature references is that the methyl group on the $N^1$ atom of the purine ring is replaced by a hydrogen atom.

An advantage of the new compounds of the Formula I is their low toxicity. As a control during the biological tests Codeine HCl and 2-(theophylline-7-yl)methyl-1,3-dioxolane were used. The antitussive activity was measured according to the method disclosed in Arzneimittel Forschung 1966, 617 on guinea pigs following a per os administration by measuring the cough relief induced by a 15 percent citric acid spray.

Both female and masculine guinea pigs weighing 300 to 350 g. were placed in a 3,000 $cm^3$ plexi inhalation box and 15 percent citric acid solution was sprayed into the box diameter: 0.4–5 micrometer. The measurement was carried out on the basis of the number of coughs within 10 minutes. The substances were administered by a stomach tube in a 0.5 percent methylcellulose suspension. On the basis of the literature references Il Farmaco Ed. Sc. 36, 201, 1981, the control substances acted as antitussive agents at an oral dose which dose is 100 mg/kg, therefore the screening tests were carried out with the same dosage. The results of the screening tests are shown in Table I.

TABLE I

Antitussive activity of 3-methyl-xanthine-7-yl-dioxolanes of formula Ia, Ib, Ic, Id and Ie and

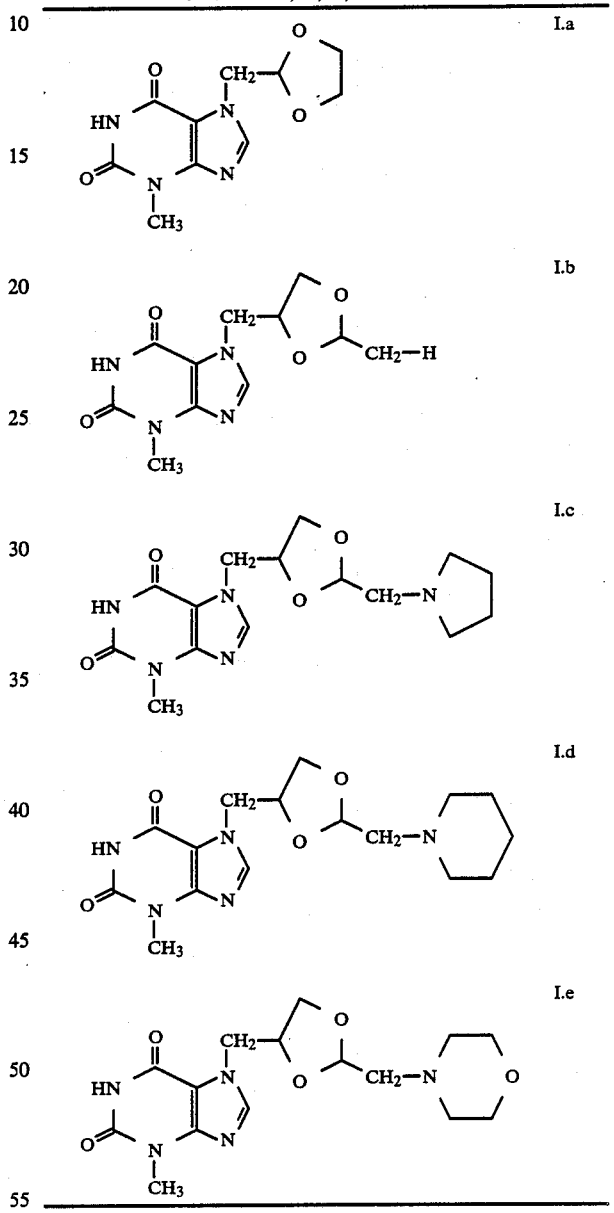

2-[(theophylline-7-yl)methyl]-1,3-dioxolane and codeine HCl, respectively, as reference compounds, after the administration of 100 mg/kg p.o. relating the cough induced in guinea pigs by a 15 percent citric acid spray to the control expressed in percents

| Dosage: 100 mg/kg p.o. | | Antitussive effect (%) Pretreatment time (h) | |
|---|---|---|---|
| Test compound | n | 1 | 4 |
| I.a. | 6 | 36.9 | 74.2 |
| I.b | 6 | 16.0 | 52.4 |

-continued

| Dosage: 100 mg/kg p.o. | | Antitussive effect (%) Pretreatment time (h) | |
|---|---|---|---|
| Test compound | n | 1 | 4 |
| I.c. HCl | 6 | 19.4 | 56.8 |
| I.d. HCl | 6 | 16.2 | 56.2 |
| I.e. HCl | 6 | 17.8 | 54.3 |
| 2-[(theophylline-7-yl)methyl]-1,3-dioxolane (reference) | 6 | 18.5 | 47.3 |
| codeine HCl (reference) | 6 | 59.8 | 48.2 |

Table I shows that during this test the most intensive cough relief effect can be observed for codeine HCl after a one hour pretreatment followed by dioxolane of the Formula I.a and the activity of the other dioxolane derivatives is much weaker.

After a four-hour pretreatment the compounds of the general Formula I exhibit a much more intensive antitussive activity than the reference substances. Of particular significance is the antitussive activity of 2-[(3-methyl-xanthine-7-yl)methyl]-1,3-dioxolane of the Formula I.a. The antitussive activity of this compound was investigated in various doses and time intervals and it could be observed that even a dose of 25 mg/kg per os results in a significant longlasting antitussive activity. As opposed to codeine HCl the compound of Formula I.a has no respiration depressing effect according to respiration function tests carried out on guinea pigs and rabbits, on the other hand the bronchopulmonal system is favorably effected. The respiration depressing and bronchus restricting activities induced by codeine, histamine and acetylcholine can be reduced proportionately to the dosage by using the compound of Formula I.a.

The compounds of the Formula I according to the invention have low toxicity. The toxicity in mice can be illustrated by the result that in case of the compounds of the Formula I.a and 2-[(teophylline-7-yl)methyl]-1,3-dioxolane none of the animals out of 12 animals was killed when using 1,000 mg/kg per os dose while the same dose caused a 100 percent mortality when using codeine HCl. The compounds of the Formula I can preferably be prepared by one of the following methods:

a, 3-methyl-xanthine of the Formula II

is reacted with dioxolane of the Formula III

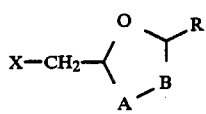

wherein
A, B and R are as given above and X stands for bromine or chlorine—in the presence of a base or
b, 2-(3-methyl-xanthine-7-yl)-acetaldehyde of the Formula IV

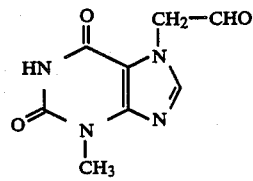

is reacted with 1,2-dihydroxyethane of the Formula V

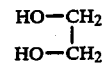

or
c, 7-(2,3-dihydroxy-propan-1-yl)-3-methyl-xanthine of the Formula VI

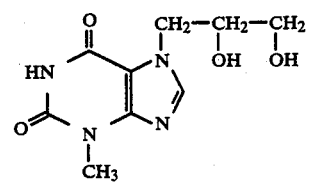

(prepared preferably according to U.S. Pat. No. 2,517,410) is reacted with acetaldehyde-diethyl-acetal of the Formula VII

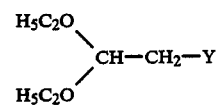

wherein Y stands for hydrogen—resulting in a compound of the Formula I.b, or Y stands for halogen preferably bromine or chlorine and in this case a compound of the Formula I.f

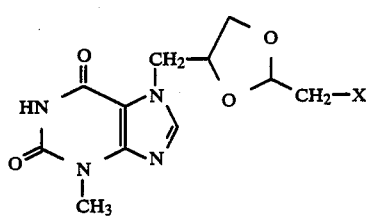

is obtained—wherein X stands for chlorine or bromine—which latter is reacted with pyrrolidine, or piperidine or morpholine and if desired a salt is formed resulting in compounds of Formula I.c-I.e.

When using process variant a, according to the invention it is preferred to use an organic solvent and/or diluent and the reaction is carried out by heating preferably at 50° to 150° C., and it is particularly preferred to carry out the reaction at the boiling point of the solvent and/or diluent.

As organic solvents and/or diluents $C_{1-4}$ alcohols, N-alkyl-acidamides particularly preferably dimethylformamide are preferred. As a base alkali- and alkali earthmetal hydroxides, alcoholates, carbonates, hydrogen-carbonates are preferred. According to a preferred variant the alkali-metal salt of 3-methyl-xanthine of the Formula II.a

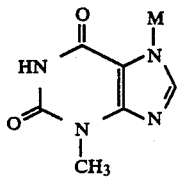

II.a wherein M stands for a potassium or sodium atom—is reacted with dioxolane of the general formula III. The reaction can be promoted if it is carried out in the presence of catalytical amount of iodide, preferably potassium iodide or sodium iodide.

Process variant b, of the invention can be performed by reacting the components in the presence of an apolar organic solvent and/or diluent preferably benzene, chlorobenzene, particularly preferably toluene or xylene and in the presence of an acid catalyst, preferably benzene sulphonic acid, toluenesulphonic acid, sulphosalicylic acid, and particularly preferably an acid synthetic resin such as DOWEX 50 W, Nafion H by heating. The reaction can be carried out by heating under pressure as well. If the reaction is not carried out under pressure, the formed water can be continuously removed by using a suitable head.

Process variant c, can be performed under similar conditions like variant b,.

If Y stands for halogen, then the exchange of halogen for amine can be performed in an organic solvent and/or diluent in the presence of an organic or in organic base. As a solvent apolar solvents, preferably benzene, toluene, chlorobenzene or protic solvents, preferably $C_{2-4}$ alcohols can be used.

The reactions are preferably performed under heating at a temperature ranging from 70° to 150° C. The reaction can be promoted by using pressure and heating.

According to another preferable embodiment of the invention is to perform the halogen amine exchange in a dipolar aprotic solvent, particularly preferably in dimethylformamide. As an inorganic base potassium carbonate is preferred. As an organic base tertiary amines, preferably triethylamine or the reacting cyclic secondary amine itself can be used and in this case the base is used in excess.

If the compounds of the Formula I contain an amine group, then acid addition salts can be formed with inorganic or organic physiologically acceptable acids. As an inorganic acid hydrochloric acid, sulphuric acid and as organic acids tartaric acid, maleic acid, lactic acid, citric acid, ascorbic acid, benzoic acid and hydroxybenzoic acid are preferred.

Salts can be formed from the compounds of the Formula I also with bases such as alkali metals and alkali earth metals, preferably sodium, potassium, calcium, magnesium etc. or complex salts may be used e.g. with ethylene diamine.

The compounds of the formula I can be used as such or admixed with pharmaceutically acceptable carriers in the form of pharmaceutical compositions. The pharmaceutical compositions can contain 0.1 to 100% active ingredient preferably 1 to 40% of active ingredient.

The daily dose may be 5 to 2,000 mg depending on the route of administration, on the age and weight of the patient. The details of our invention are illustrated by the following non-limiting examples.

EXAMPLE 1

16.6 g 3-methyl-xanthine (Chem. Ber. 83, 209, 1950) and 32.6 cm³ 10% sodium hydroxide solution are shaken to give a solution which crystallizes quickly. Water is distilled off at reduced pressure and the traces of water are removed by a toluene azeotropic distillation. The residue is suspended in 250 cm³ dimethyl formamide whereafter 16.7 g 2-bromo-methyl-1,3-dioxolane (Chem. Ber. 97, 827; 1964) and 0.5 g of potassium iodide are added and the mixture is maintained for 12 hours at 110°–118° C. The solvent is distilled off at reduced pressure and the residue is mixed with 100 cm³ of water, distilled by suction and washed with water. Upon crystallizing from propanol 17.0 g (68%) 2-[(3-methyl-xanthine-7-yl)methyl]-1,3-dioxolane of the formula I.a are obtained. Melting point is: 277°–279° C. Mass: M+ =252.

| $^1$H-NMR (DMSO $d_6$) | | |
|---|---|---|
| 3.4 ppm | s 3H | NCH$_3$ |
| 3.85 ppm | s 4H | $-CH\begin{matrix}O-CH_2\\ \mid \\ O-CH_2\end{matrix}$ |
| 4.4–4.45 ppm | d 2H | —CH$_2$— |
| 5.1–5.25 ppm | t 1H | $-CH\diagup\diagdown$ |
| 8.0 ppm | s 1H | 8CH |
| 11.15 ppm | s 1H | NH |

EXAMPLE 2

20.8 g 2-(3-methyl-xanthine-7-yl)-acetaldehyde (Formula IV)-prepared similarly like 7-theophyllinyl acetaldehyde Il Farmaco, Ed. Sc. 17, 73; (1962), 40.0 ethylene glycol (Formula II) 2.5 g DOWEX 50 W synthetic resin and 1,000.0 cm³ toluene are heated under stirring in a flask equipped with a water condenser and a cooler until water condensation ceases. The reaction mixture is filtered hot and the precipitate is washed with hot toluene and the filtrate is washed upon cooling with 5% sodium hydrogen carbonate and the organic layer is evaporated after drying. The residue is crystallized three times from propanol and 2-[(3-methyl-xanthine-7-yl)methyl]-1,3-dioxolane is obtained with a yield of 55%, melting point 276°–278° C.

EXAMPLE 3

12.0 g 7-(2,3-Dihydroxy-propan-1-yl)-3-methyl-xanthine (U.S. Pat. No. 2,517,410), 12.0 g diethyl acetal, 0.5 g sulphosalicylic acid anhydride are triturated to give a mass which is heated in a flask equipped with a distillation head at 135° C. until the distillation of ethanol is terminated. After cooling the mixture is thoroughly washed with a 5% sodium hydrogen carbonate solution and it is repeatedly decanted and the obtained mass is extracted in an extraction equipment with chloform until the dissolution of the organic substance is ceased. After drying chloroform is distilled off. The residue is crystallized from ethanol and 7.2 g (54%) of 2-methyl-4-[(3-methyl-xanthine-7-yl)methyl]-1,3-dioxolane are obtained. M.p.: 255°–260° C.

EXAMPLE 4

A triturated mass of 24.0 g 7-(2,3-dihydroxy-propan-1-yl)-3-methyl-xanthine, 30.4 g of chloroacetaldehyde-diethylacetal, 1.0 g sulfosalicylic acid anhydride is heated at 140° C. equipped with distillation attachment until the distillation of ethanol is terminated. The mixture is neutralized with an 5% sodium hydrogen carbonate solution and extracted with chloroform in a recirculatory extraction equipment, the chloroform solution is evaporated after drying and the residue is throroughly distilled off by suction and dissolved in 300 cm$^3$ dimethyl formamide and heated in a sealed flask together with 100.0 g of pyrrolidine at 100° C. for 24 hours. The excess of pyrrolidine and the solvent are distilled off at reduced pressure and the residue is thoroughly washed with water, dried and boiled for 10 minutes together with 500 cm$^3$ ethanol and acidified after filtration in cold state with ethanol containing hydrochloric acid. The mixture is allowed to stand in refrigerator, the crystals are isolated by suction and washed with ethanol thoroughly and crystallized from ethanol three times. After drying at 100° C. 15.6 g (42%) 2-pyrrolidino-methyl-4-[(3-methylxanthine-7-yl)methyl]-1,3-dioxolane hydrochloride of the Formula I.c are obtained.

EXAMPLE 5

Similar starting materials are used as in Example 4 but dimethyl formamide is replaced by toluene and 2-pyrrolidinomethyl-4-[(3-methyl-xanthine-7-yl)methyl]-1,3-dioxolane hydrochloride of the Formula I.c are obtained with a yield of 35%.

EXAMPLE 6

A triturated mass of 12.0 g 7-(2,3-dihydroxy-propan-1-yl)-3-methyl-xanthine, 15.2 g of chloro-acetaldehyde diethylacetal, 0.5 g NAFION-H catalyst is heated at 140° C. until ethanol is distilled off and the procedure in Example 4 is followed and after evaporation the mixture is heated in 150 cm$^3$ dimethyl formamide with 7.0 g potassium carbonate and 7.2 g of pyrrolidine at 80° C. for 48 hours, the mixture is evaporated, washed with water and after ethanolic salt formation 2-pyrrolidinomethyl-4-[(3-methylxanthine-7-yl)methyl]-1,3-dioxolane hydrochloride of the Formula I.c is obtained with a yield of 25%.

EXAMPLE 7

One may proceed as disclosed in Example 4 but pyrrolidine is replaced by piperidine at similar weight ratio and 2-piperidino-methyl-4-[(3-methyl-xanthine-7-yl)methyl]-1,3-dioxolane hydrochloride of the Formula I.d is obtained.

EXAMPLE 8

One may proceed as disclosed in Example 4 but pyrrolidine is replaced by morpholine at similar weight-ratio and 2-morpholino-methyl-4-[(3-methyl-xanthine-7-yl)methyl]-1,3-dioxolane hydrochloride of the Formula I.e is obtained with a yield of 31%.

EXAMPLE 9

Pharmaceutical Compositions a, Tablets:

| | |
|---|---|
| 2-[(3-methyl-xanthine-7-yl)methyl]-1,3-dioxolane | 15.0 g |
| Wheat starch | 125.0 g |
| Calcium phosphate | 199.0 g |
| Magnesium stearate | 1.0 g |
| Total: | 340.0 g |

The pulverized mixture is pressed to 1,000 pieces or tablets weighing 340 mg and containing 15 mg active ingredient each.

b, Syrup:

| | |
|---|---|
| 2-[(3-methyl-xanthine-7-yl)methyl]-1,3-dioxolane | 7.5 g |
| Lemon syrup | 200.0 cm$^3$ |
| Benzoic acid solution | 20.0 cm$^3$ |
| Water | 100.0 cm$^3$ |
| Sugar syrup | 1,000.0 cm$^3$ |

The active ingredient is dissolved in water while hot and 500 cm$^3$ of sugar syrup is added and the other components are also added and the mixture is filled up to 1,000 cm$^3$ with sugar syrup.

Each cm$^3$ of syrup contains 7.5 mg of active ingredient.

We claim:

1. A compound of the Formula (I)

or a physiologically acceptable salt thereof
wherein
A and B are each either oxygen or —CH$_2$—;
R is either hydrogen or —CH$_2$—Q; and
Q is hydrogen, pyrrolidino, piperidino, or morpholino;
  with the proviso that if A is oxygen, then B is —CH$_2$— and
R is hydrogen, and with the further proviso that if A is —CH$_2$—, B is oxygen, and R is —CH$_2$—Q where Q is hydrogen, pyrrolidino, piperidino or morpholino.

2. A method of treating a cough in a mammalian subject comprising the step of administering to said subject a therapeutically effective amount of the compound of the Formula (I) as defined in claim 1 or a physiologically acceptable salt thereof.

3. 2-[(3-methyl-xanthine-7-yl)-methyl]-1,3-dioxolane as defined in claim 1.

4. 2-methyl-4-[(3-methyl-xanthine-7-yl)methyl]-1,3-dioxolane as defined in claim 1.

5. 2-pyrrolidino-methyl-4-[(3-methyl-xanthine-7-yl)methyl]-1,3-dioxolane as defined in claim 1.

6. 2-piperidino-methyl-4-[(3-methyl-xanthine-7-yl)methyl]-1,3-dioxolane as defined in claim 1.

7. 2-morpholino-methyl-4-[(3-methyl-xanthine-7-yl)methyl]-1,3-dioxolane as defined in claim 1.

8. An antitussive pharmaceutical composition comprising as active ingredient a therapeutically effective amount of the compound of the formula I or a physiologically acceptable salt thereof, as defined in claim 1, in combination with a pharmaceutically acceptable inert carrier.

* * * * *